United States Patent [19]

Aspnes et al.

[11] 4,332,833

[45] Jun. 1, 1982

[54] METHOD FOR OPTICAL MONITORING IN MATERIALS FABRICATION

[75] Inventors: David E. Aspnes; Brian G. Bagley, both of Watchung, N.J.

[73] Assignee: Bell Telephone Laboratories, Incorporated, Murray Hill, N.J.

[21] Appl. No.: 126,217

[22] Filed: Feb. 29, 1980

[51] Int. Cl.³ ............................................. H01L 21/66
[52] U.S. Cl. ................................. 427/8; 29/574; 156/601; 156/626; 156/627; 204/192 SP; 324/71 R; 324/71 SN; 427/9; 427/10; 427/85; 427/86; 427/88; 427/91; 427/93; 427/94; 427/95; 427/99; 427/248.1; 430/30; 430/311
[58] Field of Search ................... 29/574; 427/8–10, 427/86, 99, 85, 88, 91, 93–95, 248.1; 156/601, 626, 627; 204/192 SP; 324/71 R, 71 SN; 430/30, 311

[56] References Cited

U.S. PATENT DOCUMENTS 4,197,632  4/1980  Aomura ............................... 29/574

OTHER PUBLICATIONS

Scientific American, Sep. 1977, pp. 111–128.
IEEE Transactions on Parts, Hybrids, and Packaging, vol. PHP 10(4), pp. 221–229, Dec. 1974.
Semiconductor Silicon 1977, pp. 241–252, 360–366, 422–430.
Solid State Technology, Feb. 1978, pp. 43–44 and 47.
Microelectronics J. (GB), vol. 9(3), pp. 27–30, (1979).
Opt. Spectrosc. (USSR), vol. 45(1), pp. 58–62, Jul. 1978.
Surface Technology, vol. 6, pp. 81–110, (1977).
IBM Technical Disclosure Bulletin, vol. 20(3), pp. 1242–1246, Aug. 1977.
Phys. Stat. Sol. (a), vol. 53(1), pp. 321–325, (1979).
J. Applied Physics, vol. 50(b), pp. 4196–4200, (Jun. 1979).
Ellipsometry and Polarized Light (1977), (Title Page).
Optics Communication, vol. 8(3), pp. 222–225, Jul. 1973.
J. Opt. Soc. America, vol. 66(9), pp. 949–954, Sep. 1976.
Bulletin of the American Physical Society, vol. 24(3), p. 363, (Mar. 1979).
J. Vac. Sci. Technol. 16(2), Mar./Apr. 1979, p. 216.
Optical Properties of Solids (1972), F. Abeles, ed., (Title Page).
Optical Properties of Solids: New Development, B. O. Seraphin, ed. (1976), pp. 801–845.
Journal of the Optical Society of America, vol. 65(11), Nov. 1975, pp. 1274–1278.
Applied Optics, vol. 14(1), pp. 220–228, Jan. 1975.
Physical Review B, vol. 20 (8), Oct. 15, 1979, pp. 3292–3302.

Primary Examiner—John D. Smith
Attorney, Agent, or Firm—Peter V. D. Wilde; Richard D. Laumann

[57] ABSTRACT

It has been found that the dielectric function $\epsilon(\nu)$ of materials is strongly dependent on the microstructure of the material, i.e., on the volume fractions that are crystalline, amorphous, and void, respectively. This sensitivity makes it possible to conveniently and nondestructively determine by optical methods, typically a form of spectroscopic ellipsometry, the microstructure of layers of material that are typically bounded by a free surface. The determination of actual volume fractions is made by fitting the result of a model calculation, typically in an effective medium approximation, to the measured dielectric function over an appropriate range of frequencies, e.g. frequencies corresponding to photon energies of approximately 1.5 eV–6 eV. Alternatively, the measured dielectric function, or selected features or functions thereof, can be compared to preselected standard values. In either case, if this is done in a manufacturing context then the information derived allows appropriate adjustment of some manufacturing parameter or step. This can for instance be done by means of in situ monitoring and feedback, or by means of measurements after completion of the deposition of the material, resulting in the ability to tailor subsequent processing steps to the actually existing material state. The method is applicable to dielectrics, doped and undoped semiconductors, and to metals.

20 Claims, 9 Drawing Figures

METHOD FOR OPTICAL MONITORING IN MATERIALS FABRICATION

BACKGROUND OF THE INVENTION

1. Technical Field

This invention relates to a method for obtaining information on the microstructure of non-monocrystalline matter, and of using this information to control a manufacturing process.

2. Prior Art

Although semiconductor devices generally are based on monocrystalline material, such as, for instance, epitaxial silicon, they typically require also the presence of non-monocrystalline matter, e.g., amorphous or polycrystalline insulating, semiconducting, or conducting layers, and polycrystalline metal layers. This is especially true in the case of integrated circuits (IC) in the currently practiced form of large scale integration. See, for instance, the article by W. G. Oldham, "The Fabrication of Microelectronic Circuits," *Scientific American*, pp. 111–128 (September 1977). As an example, in recent years polycrystalline silicon, deposited typically by chemical vapor deposition (CVD), has become of importance in many semiconductor applications. For instance, sub-micron thick films of polycrystalline silicon are used in silicon-gate MOS integrated circuits, and high-resistivity polysilicon films are used to control the potential and fields in high-voltage devices. See T. I. Kamins, *IEEE Transactions on Parts, Hybrids, and Packaging*, PHP-10(4), pp. 221–229 (1974). Under these circumstances it is clearly desirable to have available a reliable, fast, convenient, and non-destructive method for determining at least those properties of non-monocrystalline films, especially polysilicon films and the like, that are known to affect processing behavior and perhaps also device performance.

Contact-free conductivity and Hall angle measurements can be carried out that give information on carrier mobility, defect density, carrier concentration, and the like, and that substantially fulfill the above criteria. Similarly, contact-free capacitance techniques can be used for characterizing oxide films and oxide-semiconductor interfaces. For a review of electrical diagnostic techniques, see, for instance, W. M. Bullis and F. G. Vieweg-Gutberlet, *Semiconductor Silicon* 1977, H. R. Huff and E. Sirth, ed., The Electrochemical Society, pp. 360–366 (1977). It is also possible to determine non-destructively, by optical methods, film thickness and refractive index, the latter being typically equivalent to a composition determination. See, for instance, R. J. Kutko, *Solid State Technology*, pp. 43, 44 and 47 (February 1978), D. I. Bilenko et al, *Optics and Spectroscopy*, (USSR), Volume 45, (1), pp. 58–62 (July 1978), and D. Davies and W. A. Popov, *Microelectronics J. (GB)*, Vol. 9(3), pp. 26–30 (1979). However, it appears that no practical non-destructive method exists for determining such an important characteristic of polycrystalline films as their microstructure. Reflection x-ray scattering allows non-destructive determination of the average crystallite size, but it can not give information on the density of the reflecting material. It is typically not a thin-film characterization technique, since x-rays are usually highly penetrating, and is therefore of low accuracy in thin films. The usual current method of grain size determination is transmission electron microscopy, but x-ray or electron scattering in transmission are also possible methods, that require, however, typically a model calculation to get information on grain size. These three methods require extensive sample preparation and are typically slow and inconvenient, in addition to not being non-destructive. Also, it should be pointed out that methods involving direct observation of the structure within a small area are often unreliable since there exists no assurance that the observed area is representative of the whole. The recently developed technique of acoustic microscopy could, in principle, non-destructively provide information on the microstructure of polycrystalline films, however, in practice the resolution is insufficient. See C. F. Quate, *Semiconductor Silicon* 1977 (op. cit.) pp. 422–430.

In addition to crystallite size there is another parameter of interest in the determination of microstructure, namely, the density of the material, or, equivalently, the void fraction in the material. Currently, this parameter is typically determined by observing the reduction in thickness of a film after heat treatment. Not only is this method inconvenient and slow, and undesirable for actual IC wafers because of possible mass transport of dopants during the heat treatment, but the method is typically incapable of reliably determining the actual void fraction since there generally exists no independent assurance that the void fraction in the film after heat treatment is zero.

Thus, there appears to exist no prior art method that would allow accurate non-destructive routine determination of the volume fractions of material underlying a free surface that are respectively polycrystalline, amorphous, and void. Yet it would be highly desirable to have available a capability for determining these parameters, since it has been found that processing behavior often depends substantially on these fractions. For instance, the optical properties of polysilicon surfaces vary with the microstructure of the material, where by "microstructure" we mean the structure of the material on the scale of approximately $10\ \text{Å} - 1\ \mu\text{m}$. In practice, the microstructure of a material may contain amorphous, crystalline, and void components, or a mixture of these. For instance, during semiconductor processing it is typically required to expose a layer of photoresist on a polycrystalline layer to some appropriate radiation. It is easy to see that variations in microstructure between batches or within a batch of semiconductor wafers would, because of the dependence of the optical properties on microstructure, lead to undesirable variation in the optimum exposure time. This has been found in practice to be a serious problem for which no good solution exists, since accurate determination of reflectance is in practice a rather difficult measurement that cannot be carried out routinely on a large number of wafers. As another example, during IC fabrication it is typically necessary that parts of a previously deposited polycrystalline layer be removed by chemical etching. It has been found that the microstructure has a profound influence on etch rate. Not only is the etch rate of, for example, amorphous silicon only a small fraction of that of polycrystalline silicon, but it has been found that apparently there exists a threshold value of polycrystalline volume fraction at which etch rate appears to drop step-function-like. It probably does not require emphasis that knowledge of etch rates and, more generally, etching behavior, is crucial for instance for IC manufacture. And, as a last example, the conductivity of doped polysilicon depends strongly and nonlinearly on grain size, requiring the ability to control, and therefore to measure, grain size. See J. Y. W. Seto, ibid, pp. 241-252.

From the above, it is obvious that availability of a reliable, fast, and non-destructive method for determining the microstructure of matter would be of great advantage for instance in semiconductor fabrication, and can be expected to lead to improvements in yield, and, therefore, to more economical manufacture of devices of improved performance.

SUMMARY OF THE INVENTION

We have discovered an unexpectedly strong dependence of the dielectric function of many materials of interest in semiconductor fabrication on the microstructure of the material. This dependence allows determination of the respective polycrystalline, amorphous, and void volume fractions of a layer of material that is adjacent to a free surface, or covered by a thin transparent film, with a sensitivity high enough to permit distinction between amorphous material and polycrystalline material down to a crystallite size where any distinction between crystalline and amorphous becomes meaningless, i.e. crystallite size of the order of 20 Å. This can be done non-destructively, reliably and quickly. Although quantitative values of volume fractions determined may be slightly model-dependent, when used in a comparative mode the inventive method gives unambiguous results. The method makes it possible to monitor, in situ, the deposition of a layer of material, or the results of a treatment step such as heat treatment, thereby creating the possibility of process control by means of a feedback loop. On the other hand, it is possible to perform the measurement on all or some of the wafers within a batch after completion of the appropriate process step, permitting perhaps a go/no-go judgment, or appropriate tailoring of subsequent process steps. Furthermore, because the method is also capable of providing information on surface condition and configuration, it can be used, for instance, to monitor surface cleaning processes in any ambient, as well as to assess surface damage, for instance from a polishing operation. It is also possible to use the method for determining the average dopant implantation depth in ion implanted material.

The inventive method comprises determining, typically by an optical method such as spectroscopic ellipsometry, the dielectric function of the material over an appropriate frequency range. The measured dielectric function, or an appropriate mathematical function thereof, can be compared with a predetermined standard, resulting in the above indicated control possibilities. Alternatively, a model calculation can be used to determine the microstructure of the sample by means of a best-fit procedure. For many substances the appropriate frequency regime corresponds to photon energies of from about 1.5 eV to about 6 eV, although, in principle, the probe radiation could be of any convenient frequency for which instrumentation is available.

The ability to determine the presence of structure having a typical dimension of 20 Å with probe radiation having a typical wavelength of 1000 Å or more appears surprising, since it is a well known rule that resolution can not be less than approximately the wavelength of the probe radiation used. However, the high sensitivity of our method is due to the fact that the polarization of matter, and, therefore, the dielectric function of matter, is determined by the electronic wave functions of the material. Since, typically, in nonmetals these wave functions have a coherence length of the order of the dimension of the microstructure, it is this length that sets the lower limit of resolution, rather than the wavelength of the probe radiation used.

DETAILED DESCRIPTION

An important aspect of our invention is the discovery that the dielectric function of many materials is a sensitive function of the microstructure of the material. The theory of the optical properties of materials is well known and therefore we will not review it here in any detail. It is extensively treated in *Optical Properties of Solids*, F. Abeles, ed., North-Holland Publ. Co., Amsterdam, London (1972), and briefly reviewed by D. E. Aspnes in *Optical Properties of Solids: New Developments*, B. O. Seraphin, ed., pp. 800-845, North Holland, Amsterdam (1976). We merely want to point out that the dielectric function $\epsilon(\nu)=\epsilon_1(\nu)+i\epsilon_2(\nu)$ describes the polarizability of matter, and the polarization is equal to the charge on a particle times the quantum-mechanical expectation value of its displacement from equilibrium (in unit applied electric field), summed over all the charge in unit volume. It is this expectation value that is sensitive to the properties of the electronic wave function, which is thus the ultimate reason for the sensitivity of the dielectric function to the microstructure of matter.

It is common practice to discuss dielectric functions in terms of oscillator strength. This terminology refers to the fact that, for many purposes, matter can be considered to be made up of a collection of one or more sets of harmonic oscillators, each set having a distinct resonance frequency. These resonance frequencies of course correspond to transition frequencies between atomic levels or electronic bands in the actual material. General rules exist that can often be used to relate the dielectric function of a material in one region of the spectrum to that in nearby spectral regions. For instance, if $\epsilon_1 > 1$ at a particular energy then most of the oscillator strength of the system lies above that energy, otherwise, most of the oscillator strength occurs at lower energies. For metals, free carrier absorption at low energies typically predominates, and $\epsilon_1 < 1$ throughout the optical spectrum. These intraband transitions thus affect the dielectric function in the optical regime. However, in some metals, in particular the noble metals, interband transitions from the d-band to the Fermi surface occur in the visible-near uV part of the spectrum, resulting in considerable oscillator strength around these energies. Semiconductors and insulators tend to have $\epsilon_1 > 1$ in the infrared region, since absorption in these systems is dominated by valence to conduction band transitions at higher energies. In dielectrics, these transitions typically require greater than optical energies. For instance, $SiO_2$ has peak oscillator strength at about 10 to 12 eV. In semiconductors, the peak oscillator strength for transitions between valence and conduction bands typically occurs at optical energies, for instance, in Si at about 4.2 eV, and in GaAs at about 4.8 eV. In amorphous semiconductors, these transitions are broadened, and the oscillator strength shifted the lower energy, for example, 3.6 eV for Si, and 3.1 eV for GaAs. Moreover, the dielectric functions of amorphous semiconductors do not show any distinct features. Doped monocrystalline semiconductors typically also show reduced structure in $\epsilon(\nu)$ in the optical range, due to reduced long range order. We will later illustrate these effects, and show how these differences can be used to gain information on the microstructure of matter.

Although, in principle, our invention is not limited to the application of any particular method for obtaining the dielectric function, in practice, we believe that currently perhaps the most advantageous method is photometric spectroscopic ellipsometry. Ellipsometry is the branch of optical spectroscopy that deals with the measurement and interpretation of the change in polarization state of a polarized beam of light that is reflected from a reflecting surface. Since an extensive body of literature exists, we will not review the technique of ellipsometry in any detail. See, for instance, R. M. A. Azzam and N. M. Bashara, *Ellipsometry and Polarized Light*, North-Holland, Amsterdam, N.Y. Oxford (1977), and D. E. Aspnes, Chapter 15 in *Optical Properties of Solids: New Developments*, (op. cit.). We have found it convenient to use a rotating analyzer ellipsometer, but, of course, other types of ellipsometers can be used. See D. E. Aspnes, *Optics Communications*, Volume 8 pp. 222–225 (1973), D. E. Aspnes and P. S. Hauge, *Journal of the Optical Society of America*, Volume 66 (9), pp. 949–954 (1976).

Without going into details, the output of a photometric spectroscopic ellipsometer of the type used by us is a detector current I(t), and it is this time-varying current or, equivalently, the voltage signal derived from it, that contains the desired information. See D. E. Aspnes, *Journal of the Optical Society of America*, Volume 65 (11), pp. 1274–1278 (1975), and D. E. Aspnes and A. A. Studna, *Applied Optics*, Volume 14 (1), pp. 220–228 (1975). The information contained in I(t) can be extracted by Fourier analyzing the signal, preferably after digitizing it. Details of this are given in the paper by Aspnes and Studna, cited above. The Fourier transformation results in the determination of two normalized Fourier coefficients from which the sample parameters are to be extracted in a further computation step. Ibid, Section III (C). The result of this is a complex reflection ratio $\rho(\nu)$, from which the dielectric function $\epsilon(\nu) = \epsilon_1(\nu) + i\epsilon_2(\nu)$ can be calculated in a straightforward manner. We will refer to the real and imaginary part of this measured dielectric function as $\epsilon_1^m$ and $\epsilon_2^m$, respectively, and it is these two quantities that contain, inter alia, information as to the microstructure of the material underlying the surface. All layers to which light penetrates contribute to the measured dielectric function, and since penetration depth is typically frequency dependent, the layer thickness sampled will show similar dependence.

It is possible to advantageously use the information on the microstructure of the material directly underlying the reflecting surface that is contained in the measured dielectric function $\epsilon^m(\nu)$ in manufacturing, in particular in semiconductor IC manufacturing. One possibility is to incorporate the ellipsometer or equivalent measuring device and the associated data acquisition and processing facility into a feedback loop, thereby acquiring the ability to control in real time a processing step such as deposition of a polycrystalline semiconductor layer. This is shown schematically in FIG. 1. Reactor 10 contains the article 11 that is being monitored. For instance, this might be a semiconductor wafer undergoing deposition of a polysilicon layer by means of CVD, low pressure chemical vapor deposition (LPCVD), sputtering, evaporation, or any other appropriate process, or of deposition of a dielectric or conductive layer by these or other appropriate processes. Reactants, diluents, and the like are introduced into the reactor in a controlled manner, and the reaction products are similarly removed. Reaction parameters such as power input, temperature, pressure, and the like, are similarly controlled. This control we mean to indicate by arrow 12'. Light source 14 produces a quasi-monochromatic plane polarized beam of light 15 of appropriate frequency that is directed at a non-normal angle of incidence onto the sample to be monitored, and, after typically undergoing a change of polarization state upon reflection, the reflected beam 16, after passing through an optical analyzer and other optical components, not shown here, is detected, for instance by a photoelectric detector 17. The time-varying output 18 of the detector is analyzed and transformed in computer 19, typically a dedicated minicomputer, resulting in computer output 20, the measured dielectric function $\epsilon^m(\nu)$. One or both components of $\epsilon^m(\nu)$, selected parts or appropriate mathematical functions thereof, such as, for instance, the first or higher derivatives of either $\epsilon_1^m(\nu)$ or $\epsilon_2^m(\nu)$ with respect to the frequency can be compared to predetermined standard values 21 of the equivalent quantities. Comparator 22 schematically indicates this comparison step. This comparison can be done electronically, such as, for instance, digitally by microprocessor or computer, or by some form of analog comparator, including a human operator. The exact manner in which comparison is carried out does not affect the scope of our disclosure, since many possibilities exist that can be implemented by those skilled in the art. The result of the comparison step is a control signal 23 which serves to modify, in controller 13, the preset standard controller settings 12.

Figure 1:
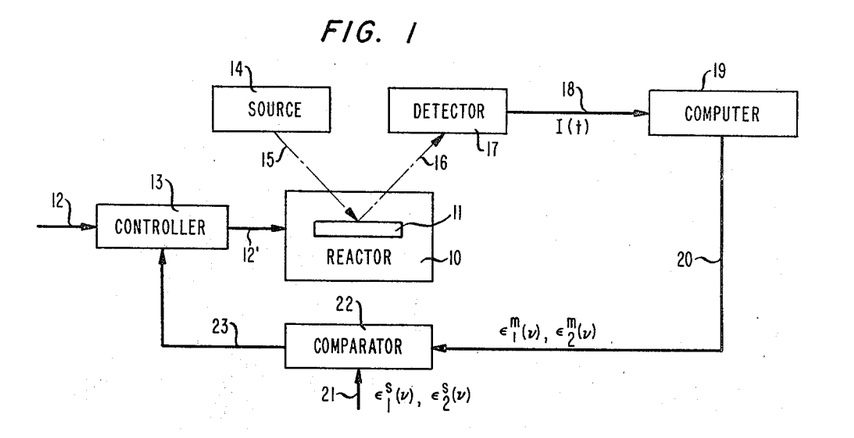
FIG. 1 shows schematically a particular application of the inventive method, namely, in a feedback loop as a process control element.

When using our invention in a feedback mode as shown in FIG. 1 then a typical sequence of events might be that $\epsilon^m$ indicates that, for instance, the volume fraction of polysilicon as deposited has dropped below a predetermined value. This could trigger an appropriate controller response, such as for instance would lead to an increase in the substrate temperature, or a decrease in the deposition rate. Similarly, an unacceptably high volume of voids could be detected, resulting in similar controller action.

Our invention can be used in other modes also. For instance, after completion of a manufacturing step during which a non-monocrystalline layer is deposited, an appropriate measurement could be made either on all samples within a given deposition run, or on selected samples only, and the values of $\epsilon^m$ obtained for the various samples could be used to either adjust individually appropriate subsequent manufacturing steps such as, for instance, exposure times or etching times. Perhaps the simplest mode of using our invention would be as a go/no-go tester that eliminates particular samples because the microstructure is such as to make these samples unacceptable for further processing. Since the dielectric function can also provide information as to surface condition, e.g. surface roughness, or surface contamination (see D. E. Aspnes, J. B. Theeten and F. Hottier, *Phys. Rev. B* 20 (8), pp. 3292-3302 (1979)), the inventive method can be used also for monitoring surface conditions and configurations, in modes similar to the ones discussed above. It could, for instance, be usefully employed in monitoring of surface cleaning processes, or to determine the extent of surface damage. These possible applications of the novel information gained are to be considered only examplary and not exclusive. We want to point out that all these applications are possible even if the material is covered by a thin transparent film, such as an oxide, although a decrease of the accuracy of the determination of volume fractions may occur under these circumstances.

Figure 2:
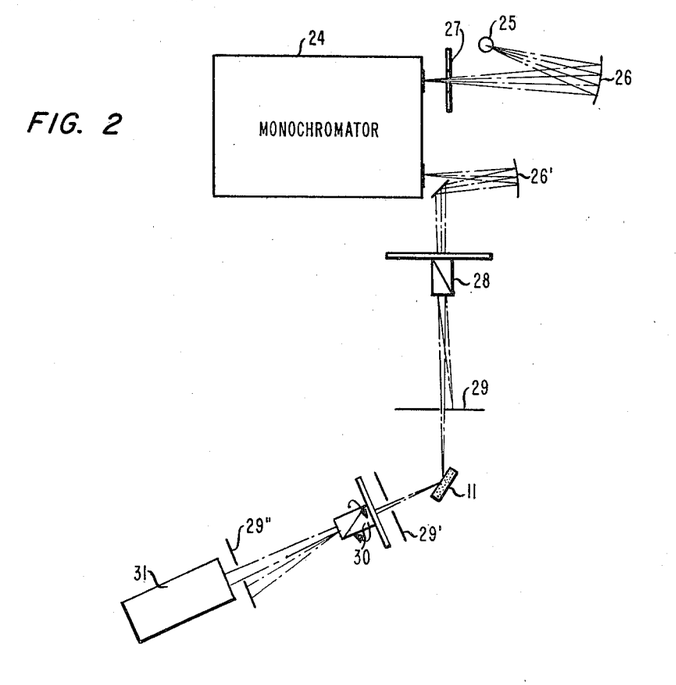
FIG. 2 shows schematically a spectroscopic ellipsometer that can usefully be employed in the practice of our invention.

In FIG. 2 we show schematically a photometric spectroscopic ellipsometer of the rotating analyzer-type that we have found useful for determining the dielectric function of materials. Lamp 25, typically a high pressure arc lamp, is the source of electromagnetic radiation. The lamp flux is focused by a mirror 26 through shutter 27 onto the entrance slit of a monochromator 24 that serves to select a narrow band of frequencies from the broadband input. The quasi-monochromatic light emerging from the entrance slit of the monochromator is collected by a second mirror 26', adjusted to focus the slit image onto the sample 11. Polarizer 28 serves to plane polarize the quasi-monochromatic beam, and aperture 29 removes the unwanted deflected beam as indicated. The light reflected from the sample surface passes through aperture 29', rotating analyzer 30, and a further aperture 29" to detector 31, typically a photomultiplier. Aperture 29' serves to reduce possible residual stray light, whereas aperture 29" is used to remove the unwanted deflected beam. The operation of such an ellipsometer is described in detail in D. E. Aspnes and A. A. Studna, *Applied Optics*, (op. cit.).

As an example of actual instrumentation, we have used a high pressure 75 watt Xe short arc lamp, and a Cary Model 14 0.5 m monochromator having a spectral resolution of 1.7 nm when operated at typical slit widths of 0.5 mm. Mirrors 26 and 26' are 30 cm focal length spherical mirrors. Both polarizer 28 and analyzer 30 are Rochon prisms of crystal quartz. The detector is an EMI 9558QB end-on photomultiplier having a useful spectral range of about 1.5-6.0 eV. The analyzer is typically rotated at 63 Hz. The monochromator setting is kept constant during the measurement at any one frequency, then changed to result in 17 meV increments. The dwell time is typically 1 sec. The instrument as described is capable of measurements in the wavelength region of interest to us, i.e., from about 207 to about 826 nm, but of course, it is possible to construct instruments covering somewhat different wavelength regimes, and the scope of our invention is in no way limited by the wavelength regime chosen.

Figure 3:
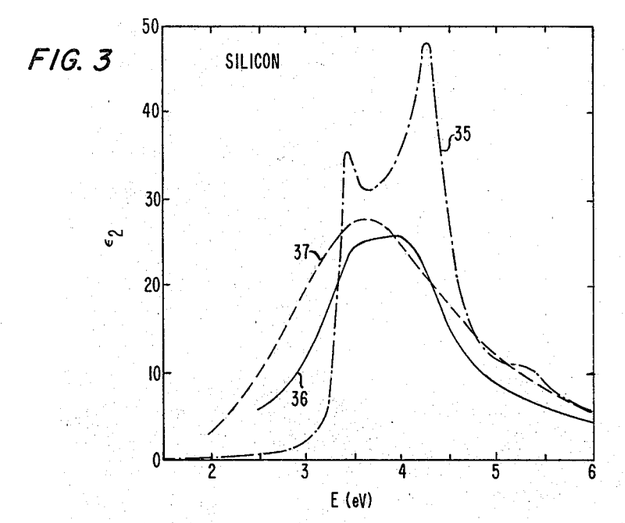
FIG. 3 shows the imaginary part of the dielectric function for single crystal silicon, amorphous silicon, and polycrystalline silicon, respectively.

In the remaining figures we give examples of measurement results to illustrate the sensitivity of the dielectric function to changes in the microstructure of matter. In FIG. 3 we show measured values of $\epsilon_2$ for monocrystalline silicon (35), amorphous silicon 37, and polycrystalline silicon of quite small average crystallite size 36. It will be noted that the abscissa is labelled in energy units. This can easily be converted into wavelengths by noticing that $E\lambda = 1.24$ eV$\mu$m, where E is the photon energy, and $\lambda$ the corresponding wavelength of light. The two pronounced peaks in 35 are due to interband transitions, and are typical of pure monocrystalline semiconductor material. 37 shows no discernable structure, indicating absence of long range order in the sample, which also results in a broadening of the range of appreciable oscillator strength. 36 is intermediate between monocrystalline and amorphous material, showing quite noticeably the beginning growth of peaks near about 3.5 eV and 4.2 eV, indicating the presence in at least some fraction of the material of long range order. We have found that the detection of the onset of polycrystallinity can be improved if $\epsilon_2$ is not used directly but rather a derivative of $\epsilon_2$ as a function of frequency. Thus, we have routinely numerically differentiated the measured dielectric functions, and have found that for our purposes the second derivative usually has sufficient sensitivity to structure in the dielectric constant to serve as a good indicator. However, the first derivative may sometimes be found useful, similarly, it may be advantageous at times to go to higher derivatives. Also, for some specialized applications a still different mathematical function of the measured dielectrical function may be found useful, and our invention is not limited by the method of data manipulation used.

Figure 4:
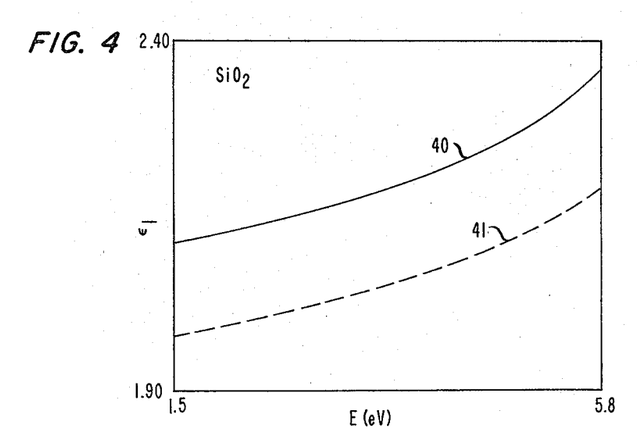
FIG. 4 shows the real part of the dielectric function of a dielectric ($SiO_2$), together with a curve calculated to show the expected change due to the presence of a ten percent void fraction in the dielectric material.

FIG. 4 shows the utility of the real part of the dielectric function for determining the volume fraction of voids in amorphous dielectrics, in this case $SiO_2$. Curve 40 is the measured $\epsilon_1$ over the energy range from 1.5 eV to 5.8 eV, and 41 is a calculated $\epsilon_1$, assuming a 10 percent density deficit, using the Bruggeman effective medium approximation. See D. E. Aspnes, J. B. Theeten, and F. Hottier, op. cit. One can see that the assumed density deficit results in approximately 13 percent reduction in $\epsilon_1$, demonstrating that the method is typically easily able to resolve about 1 percent change in density deficit or better.

Figure 5:
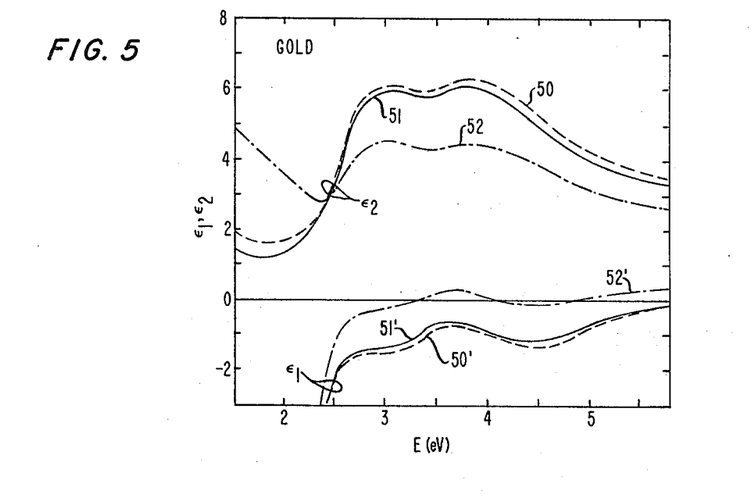
FIG. 5 shows both the real and imaginary part of the dielectric function of gold films deposited under various conditions.

FIG. 5 shows the effect of changes in microstructure on the dielectric function of a metal, in particular, on thin films (about 500 Å) of gold. The film yielding curves 50 and 50' was deposited at a substrate temperature of about 250 degrees C., that yielding curves 51 and 51' at room temperature, and that yielding curves 52 and 52' at liquid nitrogen temperature. From transmission electron microscopy we know that the low temperature film is full of voids and defects, whereas by contrast the room temperature and high temperature films are relatively close packed and differ mainly in grain size from each other. The room temperature film is fine grained, while the high temperature film has a much larger average grain size due to annealing during growth. We find that in the interband region above 2.5 eV, the most important single factor affecting the dielectric function typically is not grain size or surface roughness, but voids, and in the Drude region below 2.5 eV typically grain size effects are most important. Thus, in metals that do not have interband transitions the measurement of the dielectric function, in particular, that of $\epsilon_2$, allows convenient deduction of the average grain size and void content in films. Since electromigration is an important failure mechanism in semiconductor devices, and since this phenomenon is known to be greatly dependent on grain size and void content, it is clear that a convenient non-destructive method for determining these properties in metal film is of great importance for the semiconductor industry. In metals lacking interband transitions, measurement of the dielectric function can be used to assess crystallite size, and thus easily get a measure of this important film parameter.

Figure 6:
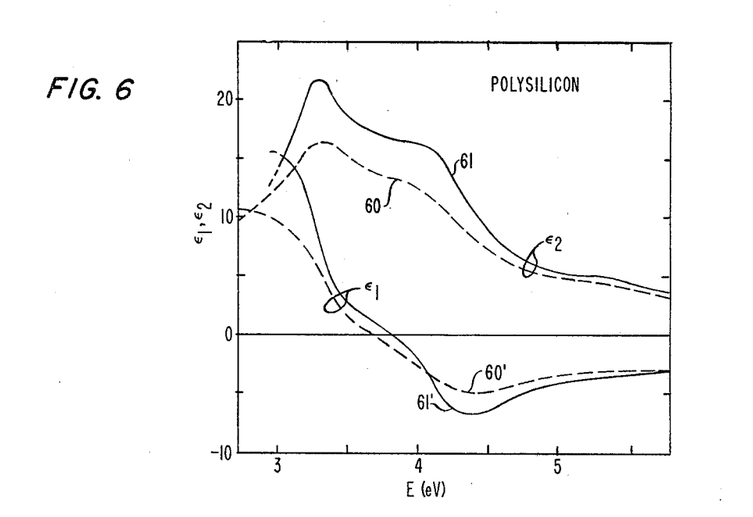
FIG. 6 shows the real and imaginary part of the dielectric function of polycrystalline silicon both before and after annealing.

FIG. 6 shows the real and imaginary part of the dielectric function for a polysilicon film, formed by LPCVD, as deposited 60 and 60', and after annealing 61 and 61'. The figure demonstrates the profound change the dielectric function undergoes upon increase in the long range order due to grain growth during annealing, that makes it easy to draw conclusions as to the microstructure from measured dielectric functions.

Figure 7:
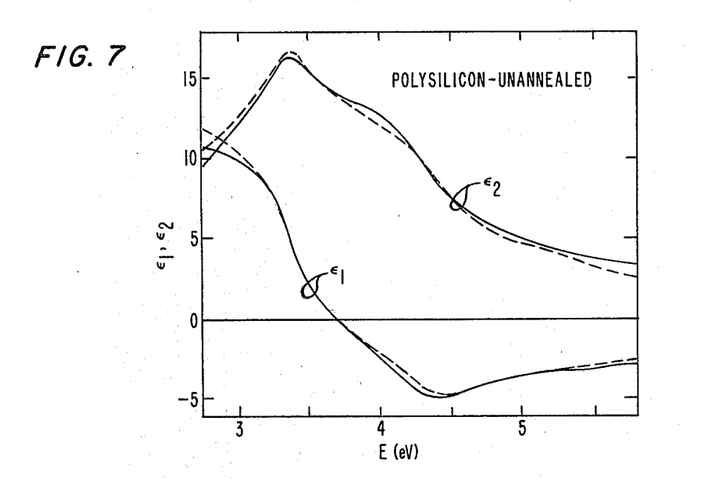
FIG. 7 shows the real and imaginary part of the dielectric function of unannealed polycrystalline silicon, together with curves calculated to give the best fit to the measured dielectric function.

FIG. 7 demonstrates the result of a curve fitting model calculation using the Bruggeman effective medium approximation, with the solid lines being the experimental result, and the dashed lines the calculated fit. The theory of effective medium models is reviewed in D. E. Aspnes, J. B. Theeten, and F. Hottier, op. cit., where a list of further references can also be found. It is there shown that, at least for the case of surface roughness on polysilicon, the Bruggeman effective medium approximation appears to give best results, but other models are available and can be used. The model calculation that resulted in the best fit to the measured curves of FIG. 7 assumed volume fractions of 0.64 amorphous silicon, 0.20 crystalline silicon, and 0.16 voids. Volume fractions determined in this manner typically will represent close approximations to the volume fractions actually present.

Figure 8:
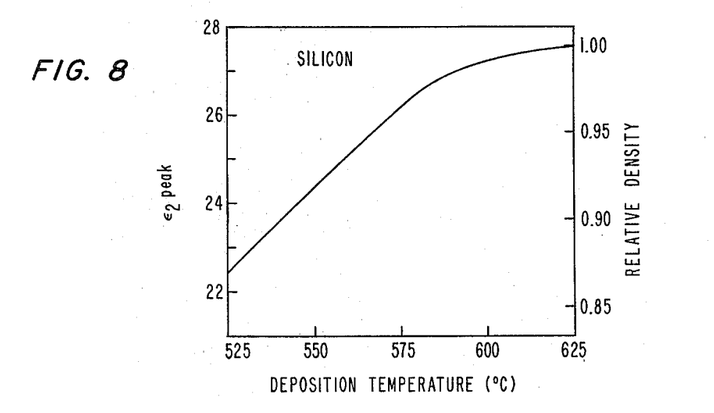
FIG. 8 shows data relating the deposition temperature of a silicon layer to the relative density of the resulting layer.

FIG. 8 shows experimental results obtained with films of silicon deposited at temperatures between 525 degrees C. and 625 degrees C. It is seen that for lower deposition temperatures the height of the peak in $\epsilon_2$ is reduced, indicating a decrease in the relative density of the material, in other words, an increase in the void fraction. This figure demonstrates the ease with which particular features of the dielectric function can be related to the microstructure of the reflecting matter.

Figure 9:
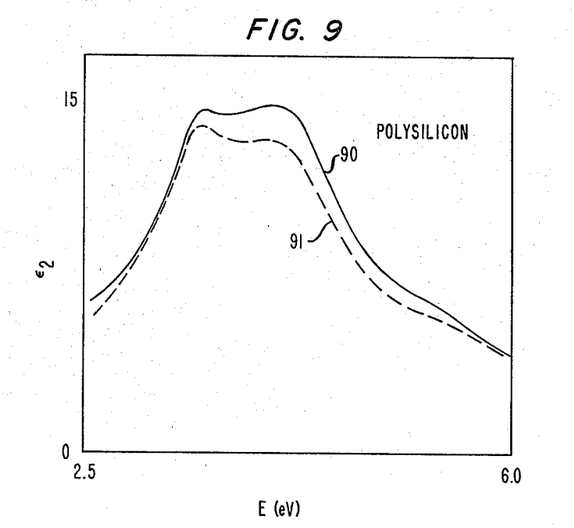
FIG. 9 shows the imaginary part of the dielectric function of two layers of polysilicon that were deposited during one and the same production onto wafers that were at different positions within the reactor vessel.

FIG. 9 shows a particularly striking example of variation in the dielectric function of two films, deposited in the same production run in an LPCVD reactor, the only difference being the position of the wafers within the reactor. Curve 90 was obtained from a wafer situated near the front, i.e., the entrance ports of the reactor, whereas curve 91 was obtained from a wafer that was near the back of the reactor vessel. The observed difference between the two wafers is due to differences in the microstructure of the polysilicon layers. This difference leads to differences in the optical properties, causing differences in the optimal exposure times for exposing a subsequent layer of photoresist.

Although the disclosure has emphasized application of the inventive method to polysilicon, which is an economically important area in which our method provides a solution to a currently existing problem, and an area which will increase in importance since the possibility of large future demand for thin silicon films for solar cells exist, the inventive method has far broader applicability. As is shown by FIGS. 4 and 5 and the accompanying remarks, the method can be used in dielectrics, of which for instance $SiO_x$ and $SiN_y$, with $0 < x \leq 2$, and $0 < y \leq 4/3$, are examples of current importance for semiconductor device fabrication, and for metals, either pure or alloys, of which currently dilute aluminum alloys such as Al(Cu) and Al(Si) as well as gold are of importance in semiconductor device manufacture. In other branches of industry however different materials may be of interest, and our method is equally applicable to them. In the manufacture of semiconductor devices application of the method is also not limited to pure i.e., undoped semiconductors, but is equally applicable to doped semiconductor material. Another class of materials of potential interest in the semiconductor industry is the metal silicides such as Ta, Co, Ti, Mo, and W silicides, and the inventive method is applicable to them also.

We claim:

1. Method for fabricating an article by a sequence of fabrication steps, one of the steps comprising forming a polycrystalline or amorphous material, the method comprising
    (a) determining a measured dielectric function $\epsilon^m(\nu)$ at a multiplicity of frequencies within a frequency range in which the dielectric function of the material $\epsilon(\nu)$ is substantially affected by interband or intraband transitions of electrons in the material,
    (b) comparing the value of a function of $\epsilon^m(\nu)$ at one or more frequencies to predetermined values, and
    (c) modifying at least one of the sequence of fabrication steps in accordance with the result of the comparison.

2. Method for fabricating an article by a sequence of fabrication steps, one of the steps comprising forming a polycrystalline or amorphous material, the method comprising
    (a) determining a measured dielectric function $\epsilon^m(\nu)$ at a multiplicity of frequencies within a frequency range in which the dielectric function of the material $\epsilon(\nu)$ is substantially affected by interband or intraband transitions of electrons in the material,
    (b) determining from $\epsilon^m(\nu)$ the volume fractions of the material that are amorphous, crystalline, and void, respectively, and
    (c) modifying at least one of the sequence of fabrication steps in accordance with the result of the determination in (b).

3. Method according to claim 1 wherein the function of $\epsilon^m(\nu)$ is a derivative of $\epsilon^m(\nu)$ with respect to frequency.

4. Method according to claim 1 wherein the function of $\epsilon^m(\nu)$ is $\epsilon^m(\nu)$.

5. Method according to claim 1 or 2 wherein the material comprises a doped or undoped semiconductor.

6. Method according to claim 5 wherein the semiconductor is silicon.

7. Method according to claim 1 or 2 wherein the material comprises a dielectric.

8. Method according to claim 7 wherein the dielectric is $SiO_x$ or $SiN_y$, with $0 < x \leq 2$, and $0 < y \leq 4/3$ 9. Method according to claim 1 or 2 wherein the material comprises a metal.

10. Method according to claim 9 wherein the metal comprises aluminum or gold.

11. Method according to claim 1 or 2 wherein $\epsilon^m(\nu)$ is determined by photometric spectroscopic ellipsometry.

12. Method according to claim 11 wherein the frequency range extends from frequencies corresponding to photon energies of approximately 1.5 eV to approximately 6 eV.

13. Method according to claim 1 or 2 wherein the temperature at which at least one of the fabrication steps is carried out is modified.

14. Method according to claim 1 or 2 wherein the flow rate of a gas in at least one of the fabrication steps is modified.

15. Method according to claim 1 or 2 wherein a time of exposure of the article to electromagnetic radiation in at least one fabrication step is modified.

16. Method according to claim 1 or 2 wherein an etching condition in at least one fabrication step is modified.

17. Method according to claim 1 or 2 wherein the material is formed by chemical vapor deposition.

18. Method according to claim 1 or 2 wherein the material is formed by low pressure chemical vapor deposition.

19. Method according to claim 1 or 2 wherein the material is formed by sputtering.

20. Method according to claim 1 or 2 wherein the material is formed by evaporation from an evaporation source.

* * * * *